US006974800B1

(12) United States Patent
Abrahamsson et al.

(10) Patent No.: US 6,974,800 B1
(45) Date of Patent: Dec. 13, 2005

(54) FORMULATIONS COMPRISING AN INHIBITOR OF CARBOXYPEPTIDASE U AND A THROMBIN INHIBITOR

(75) Inventors: Tommy Abrahamsson, Gothenburg (SE); Viveca Nerme, Västra Frölunda (SE); Magnus Polla, Gothenburg (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/600,659

(22) PCT Filed: May 3, 2000

(86) PCT No.: PCT/SE00/00847

§ 371 (c)(1),
(2), (4) Date: Jul. 20, 2000

(87) PCT Pub. No.: WO00/66152

PCT Pub. Date: Nov. 9, 2000

(30) Foreign Application Priority Data

| May 3, 1999 | (SE) | 9901572 |
| May 3, 1999 | (SE) | 9901573 |
| Aug. 13, 1999 | (SE) | 9902902 |

(51) Int. Cl.[7] .............................................. C07K 5/06
(52) U.S. Cl. .......................... 514/19; 514/18; 530/331; 562/557
(58) Field of Search .................. 514/2, 18, 19; 562/557; 530/331

(56) References Cited

U.S. PATENT DOCUMENTS

| 3,091,569 A | 5/1963 | Sheffner ........................ 167/58 |
| 3,766,206 A | 10/1973 | Hess et al. .................... 260/309 |
| 4,113,715 A | 9/1978 | Ondetti et al. ............ 260/112.5 |
| 4,177,277 A | 12/1979 | Ondetti et al. ............... 424/263 |
| 5,254,579 A | 10/1993 | Poli et al. ..................... 514/422 |
| 5,955,433 A * | 9/1999 | Bylund et al. .................. 514/19 |
| 5,993,815 A * | 11/1999 | Bajzar et al. ............. 424/145.1 |
| 6,020,510 A * | 2/2000 | Franson et al. .............. 554/224 |
| 6,126,939 A * | 10/2000 | Eisenbach-Schwartz et al. ........................ 424/185.1 |
| 6,326,386 B1 * | 12/2001 | Watson et al. ............... 514/352 |
| 6,410,587 B1 * | 6/2002 | Grainger et al. ............. 514/445 |

FOREIGN PATENT DOCUMENTS

| DE | 3838467 | 5/1990 |
| EP | 0300100 | 1/1989 |
| FR | 1393338 | 2/1965 |
| FR | 2266502 | 10/1975 |
| FR | 2430945 | 2/1980 |
| GB | 1593469 | 7/1981 |
| WO | 94/29336 | * 12/1994 |
| WO | 9616671 | 6/1996 |
| WO | WO 97/49673 | 12/1997 |

OTHER PUBLICATIONS

Bajzar, J Biol Chem 271 16603, 1996.*
Boffa, J Biol Chem 273 2127, 1998.*
Ondetti, Biochem 18, 1427, 1979.*
Current Opinion in Cardiology, vol. 12, 1997, Jonathan Alexander, MD, "Adjunctive therapy for acute myocardial infarction" p. 453-458.
U.S. Appl. No. 09/600,660 of Linschoten, et al., filed Jul. 20, 2000.
U.S. Appl. No. 09/600,661 of Linschoten, et al., filed Jul. 20, 2000.
Skidgel, R. A., "Structure and function of mamalian zinc carboxypeptidases" in *Zinc Metalloproteases in Health and Disease* N.M. Hooper, Ed., Taylor & Francis, London, pp. 241-283 (1996).
Bouma, et al, "Thrombin-Activatable Fibrinolysis Inhibitor (TAFI, Plasma Procarboxypeptidase B, Procarboxypeptidase R, Procarboxypeptidase U)," Thrombosis Res. 101, 329-354 (2001).
Zhu et al, "Isolation and characterization of americanin, a specific inhibitor of thrombin, from the salivary glands of the lone star tick *Amblyomma americanum* (L.)," Exp. Parasitol. 87, 30-38 (1997) (abstract only).
Bajzar et al., "Purification and characterization of TAFI, a thrombin-activable fibrinolysis inhibitor," J Biol Chem., 270, 14477-84 (1995) (abstract only).

* cited by examiner

Primary Examiner—David Lukton

(74) Attorney, Agent, or Firm—White & Case LLP (57) ABSTRACT

The present invention relates to pharmaceutical formulations of an inhibitor of carboxypeptidase U (CPU) and a thrombin inhibitor in admixture with a pharmaceutically acceptable adjuvant, diluent or carrier, as well as a kit of parts, a method for treatment and use of the formulations for the treatment of a condition in which inhibition of CPU and/or inhibition of thrombin are required or desired.

33 Claims, 1 Drawing Sheet

*Fig. 1*

FORMULATIONS COMPRISING AN INHIBITOR OF CARBOXYPEPTIDASE U AND A THROMBIN INHIBITOR

This application is a 371 of PCT/SE00/00847, filed May 3, 2000, which claims priority to the following Swedish patent applications: 9901572-9, filed May 3, 1999; 9901573-7, filed May 3, 1999; and 9902902-7, filed Aug. 13, 1999.

The present invention relates to pharmaceutical formulations of an inhibitor of carboxypeptidase U (CPU) and a thrombin inhibitor in admixture with a pharmaceutically acceptable adjuvant, diluent or carrier, as well as a kit of parts, a method for treatment and use of the formulations for the treatment of a condition in which inhibition of CPU and/or inhibition of thrombin are required or desired.

BACKGROUND OF THE INVENTION

Blood coagulation is the key process involved in both haemostasis (i.e. prevention of blood loss from a damaged vessel) and thrombosis (i.e. the pathological occlusion of a blood vessel by a blood clot). Coagulation is the result of a complex series of enzymatic reactions, where one of the final steps is conversion of the proenzyme prothrombin to the active enzyme thrombin.

Thrombin plays a central role in coagulation. It activates platelets, it converts fibrinogen into fibrin monomers, which polymerise spontaneously into filaments, and it activates factor XIII, which in turn crosslinks the polymer to insoluble fibrin. Thrombin further activates factor V and factor VIII in a positive feedback reaction. Inhibitors of thrombin are therefore expected to be effective anticoagulants by inhibition of platelets, fibrin formation and fibrin stabilization. By inhibiting the positive feedback mechanism they are expected to exert inhibition early in the chain of events leading to coagulation and thrombosis.

Fibrinolysis is the result of a series of enzymatic reactions resulting in the degradation of fibrin by plasmin. The activation of plasminogen is the central process in fibrinolysis. The cleavage of plasminogen to produce plasmin is accomplished by the plasminogen activators, tissue-type plasminogen activator (t-PA) or urokinase-type plasminogen activator (u-PA). Initial plasmin degradation of fibrin generates carboxy-terminal lysine residues that serve as high affinity binding sites for plasminogen. Since plasminogen bound to fibrin is much more readily activated to plasmin than free plasminogen this mechanism provides a positive feedback regulation of fibrinolysis.

One of the endogenous inhibitors to fibrinolysis is CPU. CPU is also known as plasma carboxypeptidase B, active thrombin activatable fibrinolysis inhibitor (TAFIa), carboxypeptidase R and inducible carboxypeptidase activity. CPU is formed from its precursor procarboxypeptidase U (proCPU) by the action of proteolytic enzymes e.g. thrombin, thrombin-thrombomodulin complex or plasmin. CPU cleaves basic amino acids at the carboxy-terminal of fibrin fragments. The loss of carboxy-terminal lysines and thereby of lysine binding sites for plasminogen then serves to inhibit fibrinolysis.

SUMMARY OF THE INVENTION

The present invention relates to pharmaceutical formulations containing an inhibitor of CPU and a thrombin inhibitor in admixture with a pharmaceutically acceptable adjuvant, diluent and/or carrier, as well as a method for treatment and use of the formulations for the treatment of a condition in which inhibition of CPU and/or inhibition of thrombin are required or desired.

The invention further relates to a kit of parts of vessels containing the CPU inhibitor and the thrombin inhibitor and instructions for the administration of the inhibitors to a patient in need thereof.

The invention also relates to a kit of parts of formulations containing the CPU inhibitor and the thrombin inhibitor each in admixture with a pharmaceutically acceptable adjuvant, diluent and/or carrier.

DETAILED DESCRIPTION OF THE INVENTION

It has surprisingly been found that, compared to the use of CPU and thrombin inhibitors separately, the present invention comprising a combination of a CPU inhibitor and a thrombin inhibitor potentiates anti-thrombotic effects, thereby reducing the risk for thrombosis and hypercoagulability in brood and tissues of mammals. Furthermore, the present invention offers administration of lower doses of the active ingredients, thereby reducing the risk of potential side effects of thrombin inhibitors.

In one aspect, the present invention thus relates to pharmaceutical formulations, comprising:
   (i) an inhibitor of carboxypeptidase U or a pharmaceutically acceptable salt thereof, and
   (ii) a thrombin inhibitor or a derivative thereof, in admixture with a pharmaceutically acceptable adjuvant, diluent or carrier.

A further aspect of the present invention relates to kits of parts comprising:
   (i) a vessel containing an inhibitor of carboxypeptidase U, or a pharmaceutically acceptable salt thereof;
   (ii) a vessel containing a thrombin inhibitor, or a derivative thereof; and instructions for the sequential, separate or simultaneous administration of the inhibitors (i) and (ii) to a patient in need thereof.

Another aspect of the invention relates to kits of parts comprising:
   (i) a pharmaceutical formulation containing an inhibitor of carboxypeptidase U, or a pharmaceutically acceptable salt thereof, in admixture with a pharmaceutically acceptable adjuvant, diluent or carrier; and
   (ii) a pharmaceutical formulation containing a thrombin inhibitor, or a derivative thereof, in admixture with a pharmaceutically acceptable adjuvant, diluent or carrier;
   which inhibitors (i) and (ii) are each provided in a form that is suitable for administration in conjunction with the other.

By "administration in conjunction with", we include that respective formulations comprising a CPU inhibitor and a thrombin inhibitor are administered, sequentially, separately and/or simultaneously, over the course of treatment of the relevant condition, which condition may be acute or chronic. Preferably, the term includes that the two formulations are administered (optionally repeatedly) sufficiently closely in time for there to be a beneficial effect for the patient, that is greater, over the course of the treatment of the relevant condition, than if either of the two formulations are administered (optionally repeatedly) alone, in the absence of the other formulation, over the same course of treatment. Determination of whether a combination provides a greater beneficial effect in respect of, and over the course of treatment of, a particular condition, will depend upon the condition to be treated or prevented, but may be achieved routinely by the person skilled in the art.

Thus, the term "in conjunction with" includes that one or other of the two formulations may be administered (optionally repeatedly) prior to, after, and/or at the same time as, administration with the other component. When used in this context, the terms "administered simultaneously" and "administered at the same time as" include that individual doses of CPU inhibitor and thrombin inhibitor are administered within 48 hours, e.g. 24 hours, of each other.

According to a further aspect of the invention, there is provided a method of making a kit of parts as defined herein, which method comprises bringing a component (a), as defined above, into association with a component (b), as defined above, thus rendering the two components suitable for administration in conjunction with each other.

Bringing the two components into association with each other, includes that components (a) and (b) may be:
(i) provided as separate formulations (i.e. independently of one another), which are subsequently brought together for use in conjunction with each other in combination therapy; or
(ii) packaged and presented together as separate components of a "combination pack" for use in conjunction with each other in combination therapy.

Yet another aspect of the invention relates to methods for treatment of a patient suffering from, or susceptible to, a condition in which inhibition of thrombin and/or inhibition of carboxypeptidase U are required or desired, which method comprises administering to the patient a therapeutically effective total amount of
(i) an inhibitor of carboxypeptidase U, or a pharmaceutically acceptable salt thereof, in admixture with a pharmaceutically acceptable adjuvant, diluent or carrier; in conjunction with
(ii) a thrombin inhibitor, or a derivative thereof, in admixture with a pharmaceutically acceptable adjuvant, diluent or carrier.

Still another aspect of the invention relates to methods for treatment of a patient suffering from, or susceptible to, a condition in which inhibition of thrombin and/or inhibition of carboxypeptidase U are required or desired, which method comprises administering to the patient a pharmaceutical formulation, comprising:
(i) an inhibitor of carboxypeptidase U or a pharmaceutically acceptable salt thereof, and
(ii) a thrombin inhibitor or a derivative thereof, in admixture with a pharmaceutically acceptable adjuvant, diluent or carrier.

A still further aspect of the invention relates to the use of pharmaceutical formulations, comprising:
(i) an inhibitor of carboxypeptidase U or a pharmaceutically acceptable salt thereof, and
(ii) a thrombin inhibitor or a derivative thereof, in admixture with a pharmaceutically acceptable adjuvant, diluent or carrier, in the manufacture of a medicament for the treatment of a condition in which inhibition of thrombin and/or inhibition of carboxypeptidase U are required or desired.

For the avoidance of doubt, as used herein, the term "treatment" includes therapeutic and/or prophylactic treatment.

CPU Inhibitors

Inhibitors of CPU referred to in this application include low molecular weight inhibitors of carboxypeptidase with a molecular weight below about 1000, suitably below 700.

In the present application, the CPU inhibitor is preferably
(i) a compound of general formula I, (I)

or a pharmaceutically acceptable salt or solvate thereof, or a solvate of such a salt, wherein
$R_1$ represents,
  $C_1$–$C_6$ alkyl, substituted with one or more basic groups such as amino, amidino and/or guanidino;
  cycloalkyl, substituted with one or more basic groups such as amino, amidino and/or guanidino;
  heterocyclyl, containing at least one nitrogen atom;
  heterocyclyl, containing at least one hetero atom selected from S or O, and substituted with one or more basic groups such as amino, amidino and/or guanidino;
  or aryl, substituted with one or more basic groups such as amino, amidino and/or guanidino,
$R_2$ represents H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, $Z_2N$—CO—O—, ZO—CO—NZ— or $Z_2N$—CO—NZ— group,
$R_3$ represents $COOR_5$, $SO(OR_5)$, $SO_3R_5$, $P=O(OR_5)_2$, $B(OR_5)_2$, $P=OR_5(OR_5)$, or tetrazole, or any carboxylic acid isostere,
$R_4$ represents SH, S—CO—$C_1$–$C_6$ alkyl or S—CO-aryl,
$R_5$ represents H, $C_1$–$C_6$ alkyl or aryl,
$R_6$ represents H or $C_1$–$C_6$ alkyl,
X represents O, S, SO, $SO_2$, $C(Z)_2$, N(Z), $NR_6SO_2$, $SO_2NR_6$, $NR_6CO$ or $CONR_6$,
Y represents $C(Z)_2$,
Z represents independently H, $C_1$–$C_6$ alkyl, aryl, cycloalkyl or heterocyclyl, or
(ii) a compound of general formula II (II)

or a pharmaceutically acceptable salt or solvate thereof, or a solvate of such a salt, wherein
$R_7$ represents,
  $C_1$–$C_6$ alkyl, substituted with one or more basic groups such as amino, amidino and/or guanidino;

cycloalkyl, substituted with one or more basic groups such as amino, amidino and/or guanidino;
heterocyclyl, containing at least one nitrogen atom;
heterocyclyl, containing at least one hetero atom selected from S or O, and substituted with one or more basic groups such as amino, amidino and/or guanidino;
or aryl, substituted with one or more basic groups such as amino, amidino and/or guanidino,

$R_8$ represents H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, $Z_2N—CO—O—$, $ZO—CO—NZ—$ or $Z_2N—CO—NZ—$ group, $R_9$ represents $COOR_{11}$, $SO(OR_{11})$, $SO_3R_{11}$, $P=O(OR_{11})_2$, $B(OR_{11})_2$, $P=OR_{11}(OR_{11})$, or tetrazole, or any carboxylic acid isostere,

$R_{10}$ represents a

-group, or a

-group, or a

-group, roup, $R_{11}$ represents H, $C_1$–$C_6$ alkyl or aryl,
$R_{12}$ represents $C_1$–$C_6$ alkyl, aryl, cycloalkyl, heterocyclyl, or an optionally N-substituted $H_2N—C(Z)—CONH—C(Z)—$ or $H_2N—C(Z)—$ group,
$R_{13}$ represents H or $C_1$–$C_6$ alkyl,
X represents O, S, SO, $SO_2$, $C(Z)_2$, $N(Z)$, $NR_{13}SO_2$, $SO_2NR_{13}$, $NR_{13}CO$ or $CONR_{13}$,
Y represents O, $N(Z)$, S, $C(Z)_2$, or a single bond,
Z represents independently H, $C_1$–$C_6$ alkyl, aryl, cycloalkyl or heterocyclyl,
with the proviso that when X represents O, S, SO, $SO_2$, $N(Z)$, $NR_7SO_2$, $SO_2NR_7$, or
$NR_7CO$ then Y represents $C(Z)_2$ or a single bond.

More preferred inhibitors of CPU includes compounds of general formula I, or a pharmaceutically acceptable salt or solvate thereof, or a solvate of such a salt, wherein the following individual and separate preferences apply:
$R_1$ represents,
cycloalkyl, substituted with one or more basic groups such as amino, amidino and/or guanidino;
heterocyclyl, containing at least one nitrogen atom;
heterocyclyl, containing at least one hetero atom selected from S or O, and substituted with one or more basic groups such as amino, amidino and/or guanidino;
or aryl, substituted with one or more basic groups such as amino, amidino and/or guanidino;

$R_2$ represents H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, $Z_2N—CO—O—$, $ZO—CO—NZ—$ or $Z_2N—CO—NZ—$ group, $R_3$ represents $COOR_5$,
$R_4$ represents SH, $S—CO—C_1$–$C_6$ alkyl or S—CO-aryl,
$R_5$ represents H, $C_1$–$C_6$ alkyl or aryl,
$R_6$ represents H or $C_1$–$C_6$ alkyl,
X represents O, S, SO, $SO_2$, $C(Z)_2$, $N(Z)$, $NR_6SO_2$, $SO_2NR_6$ or $CONR_6$,
Y represents $C(Z)_2$,
Z represents independently H, $C_1$–$C_6$ alkyl, aryl, cycloalkyl or heterocyclyl.

Even more preferred inhibitors of CPU includes compounds of general formula I, or a pharmaceutically acceptable salt thereof, wherein the following individual and separate preferences apply:
$R_1$ represents,
cycloalkyl, substituted with one or more basic groups such as amino, amidino and/or guanidino;
heterocyclyl, containing at least one nitrogen atom;
heterocyclyl, containing at least one hetero atom selected from S or O, and substituted with one or more basic groups such as amino, amidino and/or guanidino;

$R_2$ represents H, $C_1$–$C_3$ alkyl, amino, halogen or hydroxy,
$R_3$ represents $COOR_5$,
$R_4$ represents SH, $S—CO—C_1$–$C_6$ alkyl or S—CO-aryl,
$R_5$ represents H, $C_1$–$C_6$ alkyl or aryl,
X represents $C(Z)_2$,
Y represents $C(Z)_2$,
Z represents independently H or $C_1$–$C_6$ alkyl.

More preferred inhibitors of CPU includes compounds of general formula II, or a pharmaceutically acceptable salt or solvate thereof, or a solvate of such a salt, wherein the following individual and separate preferences apply:
$R_7$ represents,
$C_1$–$C_6$ alkyl, substituted with one or more basic groups such as amino, amidino and/or guanidino;
cycloalkyl, substituted with one or more basic groups such as amino, amidino and/or guanidino;
heterocyclyl, containing at least one nitrogen atom;
heterocyclyl, containing at least one hetero atom selected from S or O, and substituted with one or more basic groups such as amino, amidino and/or guanidino;
or aryl, substituted with one or more basic groups such as amino, amidino and/or guanidino,

$R_8$ represents H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, $Z_2N—CO—O—$, $ZO—CO—NZ—$ or $Z_2N—CO-NZ—$ group, $R_9$ represents $COOR_{11}$,

R<sub>10</sub> represents a

-group, or a

-group, or a

-group,

R$_{11}$ represents H, C$_1$–C$_6$ alkyl or aryl,
R$_{12}$ represents C$_1$–C$_6$ alkyl, aryl, cycloalkyl, heterocyclyl, or an optionally N-substituted H$_2$N—C(Z)—CONH—C(Z)— or H$_2$N—C(Z)— group,
R$_{13}$ represents H or C$_1$–C$_6$ alkyl,
X represents C(Z)$_2$,
Y represents O, N(Z), S, C(Z)$_2$, or a single bond,
Z represents independently H, C$_1$–C$_6$ alkyl, aryl, cycloalkyl or heterocyclyl.

Even more preferred inhibitors of CPU includes compounds of general formula II, or a pharmaceutically acceptable salt or solvate thereof, or a solvate of such a salt, wherein the following individual and separate preferences apply:

R$_7$ represents,
  cycloalkyl, substituted with one or more basic groups such as amino, amidino and/or guanidino;
  heterocyclyl, containing at least one nitrogen atom;
  heterocyclyl, containing at least one hetero atom selected from S or O, and substituted with one or more basic groups such as amino, amidino and/or guanidino;
R$_8$ represents H, C$_1$–C$_3$ alkyl, amino, halogen, hydroxy,
R$_9$ represents COOR$_{11}$,
R$_{10}$ represents a -group,
R$_{11}$ represents H, C$_1$–C$_6$ alkyl or aryl,
R$_{12}$ represents C$_1$–C$_6$ alkyl, aryl, cycloalkyl, heterocyclyl, or an optionally N-substituted H$_2$N—C(Z)—CONH—C(Z)— or H$_2$N—C(Z)— group, X represents C(Z)$_2$,
Y represents O or C(Z)$_2$,
Z represents independently H or C$_1$–C$_6$ alkyl.

The following definitions shall apply throughout the specification and the appended claims:

The term "basic group" denotes a basic group, wherein the conjugate acid of said basic group has a pKa of from about –5 to about 25, preferably of from 1 to 15.

The term "carboxylic acid isostere" denotes an acidic group having a pKa of from about –5 to about 25, preferably of from 1 to 15.

The term "C$_1$–C$_6$ alkyl" denotes a straight or branched, saturated or unsaturated, substituted or unsubstituted alkyl group having 1 to 6 carbon atoms in the chain wherein the alkyl group may optionally be interrupted by one or more heteroatoms selected from O, N or S. Examples of said alkyl include, but is not limited to, methyl, ethyl, ethenyl, ethynyl, n-propyl, iso-propyl, propenyl, iso-propenyl, propynyl, n-butyl, iso-butyl, sec-butyl, t-butyl, butenyl, iso-butenyl, butynyl and straight- and branched-chain pentyl and hexyl.

The term "C$_1$–C$_3$ alkyl" denotes a straight or branched, saturated or unsaturated, substituted or unsubstituted alkyl group having 1 to 3 carbon atoms in the chain wherein the alkyl group may optionally be interrupted by one or more heteroatoms selected from O, N or S. Examples of said alkyl include, but is not limited to, methyl, ethyl, ethenyl, ethynyl, n-propyl, iso-propyl, propenyl, iso-propenyl, propynyl.

The term "C$_1$ alkyl" denotes a substituted or unsubstituted alkyl group having 1 carbon atom. An example of said alkyl include, but is not limited to, methyl.

The term "C$_1$–C$_6$ alkoxy" denotes an alkyl-O-group, wherein C$_1$–C$_6$ alkyl is as defined above.

The term "C$_1$–C$_3$ alkoxy" denotes an alkyl-O-group, wherein C$_1$–C$_3$ alkyl is as defined above.

The term "heterocyclyl" denotes a substitued or unsubstituted, 4- to 10-membered monocyclic or multicyclic ring system in which one or more of the atoms in the ring or rings is an element other than carbon, for example nitrogen, oxygen or sulfur, especially 4-, 5- or 6-membered aromatic or aliphatic heterocyclic groups, and includes, but is not limited to, azetidine, furan, thiophene, pyrrole, pyrroline, pyrrolidine, dioxolane, oxthiolane, oxazolane, oxazole, thiazole, imidazole, imidazoline, imidazolidine, pyrazole, pyrazoline, pyrazolidine, isoxazole, isothiazole, oxadiazole, furazan, triazole, thiadiazole, pyran, pyridine, piperidine, dioxane, morpholine, dithiane, oxathiane, thiomorpholine, pyridazine, pyrimidine, pyrazine, piperazine, triazine, thiadiazine, dithiazine, azaindole, azaindoline, indole, indoline, naphthyridine groups, and shall be understood to include all isomers of the above identified groups. The term "azetidinyl" shall for example be understood to include the 2-, and 3-isomers and the terms "pyridyl" and "piperidinyl" shall for example be understood to include the 2-, 3-, and 4-isomers.

The term "cycloalkyl" denotes a saturated or unsaturated, substituted or unsubstituted, non-aromatic ring composed of 3, 4, 5, 6 or 7 carbon atoms, and includes, but is not limited to, cyclopropyl, cyclobutyl, cyclopentyl, cyclohexyl, cycloheptyl, cyclobutenyl, cyclopentenyl, cyclohexenyl, cycloheptenyl, cyclopentadienyl, cyclohexadienyl and cycloheptadienyl groups.

The term "halogen" includes fluoro, chloro, bromo and iodo groups.

The term "aryl" denotes a substituted or unsubstituted C$_6$–C$_{14}$ aromatic hydrocarbon and includes, but is not limited to, phenyl, naphthyl, indenyl, anthracenyl, phenanthrenyl, and fluorenyl.

The term "aryloxy" denotes an aryl-O-group, wherein aryl is as defined above.

The term "acyl" denotes an alkyl-CO-group, wherein alkyl is as defined above.

The term "aroyl" denotes an aryl-CO-group, wherein aryl is as defined above.

The term "alkylthio" denotes an alkyl-S-group, wherein alkyl is as defined above.

The term "arylthio" denotes an aryl-S-group, wherein aryl is as defined above.

The term "aroylamino" denotes an aroyl-N(Z)-group, wherein aroyl and Z are as defined above.

The term "acylamino" denotes an acyl-N(Z)-group, wherein acyl and Z are as defined above.

The term "carbamoyl" denotes a $H_2N$—CO-group.

The term "alkylcarbamoyl" denotes a $Z_2N$—CO-group wherein Z is as defined above.

The term "substituted" denotes an "$C_1$ alkyl", "$C_1$–$C_3$ alkyl", "$C_1$–$C_6$ alkyl", "cycloalkyl", "heterocyclyl", "aryl" $H_2N$—C(Z)—CONH—C(Z)— or a $H_2N$—C(Z)-group as defined above which is substituted by one or more acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, oxo, nitro, thiol, thio, $Z_2N$—CO—O—, ZO—CO—NZ—, or $Z_2N$—CO—NZ— groups.

Moreover, the compounds of Formula I wherein $R_4$ is mercapto may be present in the form of a dimer which is bonded via —S—S-bond, which is also included in this invention.

Both the pure enantiomers, racemic mixtures and unequal mixtures of two enantiomers are within the scope of the present invention. It should also be understood that all the diastereomeric forms possible are within the scope of the invention.

Depending on the process conditions the compounds of general formula I and II may be obtained either in neutral form, as salts, e.g. as pharmaceutically acceptable salts, or as solvates, e.g. as hydrates, all of which are within the scope of the present invention.

Also included in the invention are derivatives of the compounds of the formula I and II which have the biological function of the compounds of the formula I and II, respectively. For example, certain protected derivatives of compounds of formula I or II may be made prior to a final deprotection stage to form compounds of formula I and II, respectively.

The use of protecting groups is described in 'Protective Groups in Organic Synthesis', 2nd edition, T. W. Greene & P. G. M. Wutz, Wiley-Interscience (1991). The protective group may also be a polymer resin such as Wang resin or a 2-chlorotrityl chloride resin.

It will also be appreciated by those skilled in the art that, although such protected derivatives of compounds of formula I or II may not possess pharmacological activity as such, they may be administered parenterally or orally, together with the thrombin inhibitor, and thereafter metabolised in the body to form compounds of formula I or II which are pharmacologically active. Such derivatives may therefore be described as "prodrugs". All prodrugs of compounds of formula I or II are included within the scope of the invention.

In the present application, CPU inhibitors include chemical modifications, such as esters, prodrugs and metabolites, whether active or inactive, and pharmaceutically acceptable salts of any of these.

Preparation of the CPU Inhibitors of General Formula I

The CPU inhibitors of general formula I may be prepared using the following processes A–C.

Process A

Process A for manufacture of compounds with the general formula I, wherein $R_1$, $R_3$, $R_4$, and Y are as defined above and $R_2$ is H, and X is $C(Z)_2$, comprises the following steps:

a) Compounds of the general formula III, $$R1\text{-}X\text{—}OH \qquad (III)$$

wherein $R_1$, is as defined for formula I and X is $C(Z)_2$, which are either commercially available or are available using known techniques, can be converted into a compound of the general formula IV, $$R1\text{-}X\text{-}L \qquad (IV)$$

wherein L is a suitable leaving group, such as chloro, bromo, iodo, triflate or tosyl, under standard conditions using a suitable reagent, such as $PPh_3/CBr_4$, TosCl/pyridine or $(CF_3SO_2)_2O/TEA$.

b) Compounds of the general formula IV can thereafter be reacted with compounds of the general formula V, wherein $R_2$ and $R_3$ are as defined for formula I, which are either commercially available, or are available using known techniques, in the presence of a suitable base, such as $K_2CO_3$ or NaH, under standard conditions to give compounds of the general formula VI.

(c) Compounds of the general Formula VI wherein $R_1$ and $R_3$ are as defined for Formula I and X is $C(Z)_2$ and $R_2$ is H can thereafter be converted to compounds of the general Formula VII, by treatment with formaldehyde in the presence of a suitable base, such as $Et_2NH$, under standard conditions.

d) Compounds of the general formula VII can also be prepared by treating compounds of the general formula VIII, (VIII)

wherein $R_3$ and $R_5$ are as defined for formula I, with an alkylating agent of the general formula IV in the presence of a suitable base, such as LDA or NaH, under standard conditions to give compounds of the general formula IX, (IX)

e) Compounds of the general formula IX can thereafter be reacted with an appropriate aldehyde or ketone $OC(Z)_2$, in the presence of a suitable base, such as KOtBu, LDA or NaH, under standard conditions to give a compound of the general formula VII.

(VII)

f) Compounds of the general formula VII can be further reacted with compounds of the general formula X,

R5—SH    (X)

wherein $R_5$ is a suitable protecting group, such as Ac, Bz, PMB or Bn, alone or in the presence of a suitable base, such as NaOMe, NaH or triethylamine or alternatively in the presence of a free-radical initiator, such as AIBN under standard conditions to give compounds of the general formula I, wherein $R_1$, $R_3$, $R_4$, and Y are as defined for formula I and $R_2$ is H and X is $C(Z)_2$.

Process B

Process B for manufacture of compounds with the general formula I, wherein $R_1$, $R_2$, $R_3$, and $R_4$, are as defined in formula I and Y is $CH_2$, and X is O, S, SO, $SO_2$, $C(Z)_2$, or N(Z), comprises the following steps:

a) Reacting a compound of the general formula XI,

R1—X—H    (XI)

wherein $R_1$ is as defined for formula I and X is O, S, or N(Z), with an alkylating agent of the general formula XII, (XII)

wherein $R_2$ and $R_3$ are as defined for formula I and L is a suitable leaving group, such as a chloro, bromo, iodo, triflate or tosylate group, under standard conditions using suitable reagents, such as NaH, $Ag_2CO_3$, or $Bu_4NHSO_4NaOH$, to give compounds of the general formula XIII, (XIII)

b) Compounds of the general formula XIII can thereafter be reacted with carbon dioxide in the presence of a suitable base, such as LDA or KHMDS under standard conditions to give a compound of the general formula XIV, (XIV)

(c) Compounds of the general formula XIV can thereafter be reacted with an alkyl chloroformate, such as ClCOOMe in the presence of a base, such as triethylamine, and thereafter reducing the formed mixed anhydride with a suitable reducing agent, such as $NaBH_4$, under standard conditions, to give a compound of the general formula XV, (XV)

(d) Compounds of the general formula XV may thereafter be reacted with a compound of the general formula X,

R5-SH    (X)

wherein $R_5$ is a suitable protecting group, such as Ac or Bz, in the presence of a suitable reagent, such as $PPh_3$/DIAD, under standard conditions to give compounds of the general formula I, wherein $R_1$, $R_2$, $R_3$, and $R_4$ are as defined above and Y is $CH_2$ and X is O, S, $C(Z)_2$, or N(Z).

e) Compounds of the general formula I, wherein $R_1$, $R_2$, $R_3$, $R_4$ and Y are as defined above and and X is S may thereafter be reacted with a suitable oxidizing reagent, such as MCPBA under standard conditions to give compounds of the general formula I, wherein $R_1$, $R_2$, $R_3$, $R_4$ and Y are as defined above and and X is SO or $SO_2$.

Process C

Process C for manufacture of compounds with the general formula I, wherein $R_1$, $R_2$, $R_3$, $R_4$, and Y, are as defined above and X is $NR_6CO$, $CONR_6$, $SO_2NR_6$ or $NR_6SO_2$ comprises the following steps:

a) Reacting a compound of the general formula XVI, (XVI)

wherein $R_2$, $R_3$, $R_6$ and Y are as defined for formula I and $R_5$ is a suitable protecting group, such as Ac, Bz, PMB or Bn, with a compound of the general formula XVII,

R1-X  (XVII)

wherein $R_1$ is as defined for formula I and X is COOH or $SO_2Cl$ in the presence of suitable coupling reagents, such as PyBOP/DIPEA, DCC/HOBt, EDC/TEA/DMAP or pyridine under standard conditions to give compounds of the general formula I, wherein $R_1$, $R_2$, $R_3$, $R_4$, and Y, are as defined above and X is $NR_6CO$ or $NR_6SO_2$.

b) Reacting a compound of the general formula XVIII, (XVIII)

wherein $R_2$, $R_3$, and Y are as defined for formula I and X is COOH or $SO_2C_1$ and $R_5$ is a suitable protecting group, such as Ac, Bz, PMB or Bn, with a compound of the general formula XIX,

R6-NH$_2$  (XIX)

wherein $R_6$ is as defined for formula I in the presence of suitable coupling reagents, such as PyBOP/DIPEA, DCC/HOBt, EDC/TEA/DMAP or pyridine under standard conditions to give compounds of the general formula I, wherein $R_1$, $R_2$, $R_3$, $R_4$ and Y are as defined above and X is $CONR_6$ or $SO_2NR_6$.

Preparation of the CPU Inhibitors of General Formula II

The CPU inhibitors of general formula II may be prepared using the following processes D–G.

Process D

Process D for the manufacture of compounds with the general formula II, wherein $R_7$, $R_{11}$, $R_{12}$, and Z are as defined above and $R_8$ is H, $R_9$ is $COOR_{11}$, $R_{10}$ represents a -group, X is $C(Z)_2$, Y is $C(Z)_2$ and comprises the following steps:
a) Compounds of the general formula XX,

R7-X—OH  (XX)

wherein $R_7$ and Z is as defined for formula II and X is $C(Z)_2$, which are either commercially available or are available using known techniques, can be converted into a compound of the general formula XXI,

R7-X-L  (XXI)

wherein L is a suitable leaving group, such as a chloro, bromo, iodo, triflate or tosyl group, under standard conditions using a suitable reagent, such as $PPh_3/CBr_4$, TosCl/pyridine or $(CF_3SO_2)_2O/TEA$.

b) Compounds of the general formula XXI can thereafter be reacted with compounds of the general formula XXII, (XXII)

which are either commercially available or are available using known technics, in the presence of a suitable base, such as $K_2CO_3$ or NaH, under standard conditions to give compounds of the general formula XXIII, (XXIII)

(c) Compounds of the general Formula XXIII can thereafter be converted to compounds of the general Formula XXIV, (XXIV)

by treatment with formaldehyde in the presence of a suitable base, such as $Et_2NH$, under standard conditions.

However, if Y is CH(Z) then compounds of the general formula XXIV can be prepared by treating compounds of the general formula XXV, (XXV)

with an alkylating agent of the general formula XXI,

R7-X-L  (XXI)

wherein $R_7$ is as defined for formula II and L is a suitable leaving group, such as a chloro, bromo, iodo, triflate or tosyl group, in the presence of a suitable base, such as LDA or NaH, under standard conditions to give compounds of the general formula XXVI, (XXVI)

Compounds of the general formula XXVI can thereafter be reacted with an appropriate aldehyde CHO(Z), wherein Z is as defined for formula II, in the presence of a suitable base, such as KOtBu, LDA or NaH, under standard conditions to give to give a compound of the general formula XXIV.

d) Compounds of the general formula XXIV can be further reacted with compounds of the general formula XXVII $$R_{12}PO_2H_2 \quad (XXVII)$$

wherein $R_{12}$ is as defined for formula II, in the presence of a suitable reagent, such as BSA or HMDS, under standard conditions to give compounds of the general formula II, wherein $R_7$, $R_{11}$, $R_{12}$ and Z are as defined above, $R_8$ is H, $R_9$ is $COOR_{11}$, $R_{10}$ represents a

-group,

X is $C(Z)_2$, and Y is $C(Z)_2$.

Process E

Process E for manufacture of compounds with the general formula II, wherein $R_7$, $R_8$, $R_{11}$, $R_{12}$, and Z are as defined above, $R_9$ is $COOR_{11}$, X is $C(Z)_2$, Y is O, and $R_{10}$ represents a -group, comprises the following steps:

a) Reacting a compound of the general formula XXVIII, $$R7\text{-}XCO\text{-}R8 \quad (XXVIII)$$

wherein $R_7$, $R_8$ and Z are as defined in formula II and X is $C(Z)_2$ in the presence of suitable reagents, such as TMSCN/ZnI$_2$ or KCN/HOAc, under standard conditions to give compounds of the general formula XXIX,

(XXIX)

wherein $R_7$ and $R_8$ are as defined in formula II and X is $C(Z)_2$.

b) Compounds of the general formula XXIX can thereafter be treated with suitable reagents, such as HCl or HCl/MeOH, under standard conditions to give compounds of the general formula XXX, (XXX)

wherein $R_7$ and $R_8$ are as defined in formula II and X is $C(Z)_2$.

c) Compounds of the general formula XXX can thereafter be reacted with compounds of the general formula XXXI, $$R_{12}PO_3H_2 \quad (XXXI)$$

wherein $R_{12}$ is as defined in the general formula II, which are either commercially available, well known in the literature, or are available using known techniques, in the presence of suitable coupling reagents such a DCC/DMAP, PyBop/DIPEA or SOCl$_2$, under standard conditions to give compounds of the general formula II, wherein $R_7$, $R_8$, $R_{11}$, $R_{12}$ and Z are as defined above, $R_9$ is $COOR_{11}$, $R_{10}$ represents a -group,

X is $C(Z)_2$ and Y is O.

Process F

Process F for manufacture of compounds with the general formula II, wherein $R_7$ and $R_8$ are as defined above and X and Y is $C(Z)_2$ or a single bond and $R_9$ and $R_{10}$ are $COOR_{11}$, comprises the following steps, a) reacting a compound of the general formula XXXII, (XXXII)

wherein $R_8$ and $R_{11}$ are as defined in formula II and Y is $C(Z)_2$ or a single bond, which are either commercially available, well known in the literature, or are available using known techniques, with a compound of the general formula XXI, $$R7\text{-}X\text{-}L \quad (XXI)$$

wherein $R_7$ is as defined for formula II, X is $C(Z)_2$ and L is a suitable leaving group, such as Cl, Br, I or tosyl, in the presence of a suitable base, such as LDA or NaH under standard conditions, to give a compound of the general formula XXXIII, (XXXIII)

b) hydrolysing a compound of the general formula XXXIII, for example by treatment with aqueous NaOH or aqueous TFA under standard conditions to give compounds of the general formula II, wherein $R_7$ and $R_8$ are as defined above and X and Y is $C(Z)_2$ or a single bond and $R_9$ and $R_{10}$ are COOH.

Process G

Process G for manufacture of compounds with the general formula II, wherein $R_7$, $R_8$, $R_{11}$, $R_{13}$, X, Y and Z are as defined above, $R_9$ is $COOR_{11}$ and $R_{10}$ represents a -group, comprises the following steps:

a) Compounds of the general formula XXXIII, (XXXIII)

can be reacted with compounds of the general formula XXXIV, (XXXIV)

wherein $R_{13}$ is as defined in formula II, in the presence of suitable reagents, such as DCC/DMAP, under standard conditions, to give compounds of the general formula II, wherein $R_7$, $R_8$, $R_{11}$, $R_{13}$, X, Y and Z are as defined above, $R_9$ is $COOR_{11}$ and $R_{10}$ represents a -group. oup.

Thrombin Inhibitors

Thrombin inhibitors referred to in this application include but are not limited to low molecular weight thrombin inhibitors. The term "low molecular weight thrombin inhibitor" will be understood by those skilled in the art. The term may also be understood to include any composition of matter (e.g. chemical compound) which inhibits thrombin to an experimentally determinable degree in in vivo and/or in in vitro tests, and which possesses a molecular weight of below about 2,000, preferably below about 1,000.

Preferred low molecular weight thrombin inhibitors include low molecular weight peptide-based, amino acid-based, and/or peptide analogue-based, thrombin inhibitors.

The term "low molecular weight peptide-based, amino acid-based, and/or peptide analogue-based, thrombin inhibitors" will be well understood by one skilled in the art to include low molecular weight thrombin inhibitors with one to four peptide linkages, and includes those described in the review paper by Claesson in Blood Coagul. Fibrin. (1994) 5,411, as well as those disclosed in U.S. Pat. No. 4,346,078, International Patent Applications WO 93/11152, WO 93/18060, WO 93/05069, WO 94/20467, WO 94/29336, WO 95/35309, WO 95/23609, WO 96/03374, WO 96/06832, WO 96/06849, WO 96/25426, WO 96/32110, WO 97/01338, WO 97/02284, WO 97/15190, WO 97/30708, WO 97/40024, WO 97/46577, WO 98/06740, WO 97/49404, WO 97/11693, WO 97/24135, WO 97/47299, WO 98/01422, WO 98/57932, WO 99/29664, WO 98/06741, WO 99/37668, WO 99/37611, WO 98/37075, WO 99/00371, WO 99/28297, WO 99/29670, WO 99/40072, WO 99/54313, WO 96/31504, WO 00/01704 and WO 00/08014; and European Patent Applications 648 780, 468 231, 559 046, 641 779, 185 390, 526 877, 542 525, 195 212, 362 002, 364 344, 530 167, 293 881, 686 642, 669 317, 601 459 and 623 596, the disclosures in all of which documents are hereby incorporated by reference.

In the present application, derivatives of thrombin inhibitors include chemical modifications, such as esters, prodrugs and metabolites, whether active or inactive, and pharmaceutically acceptable salts and solvates, such as hydrates, of any of these, and solvates of any such salt.

Preferred low molecular weight peptide-based thrombin inhibitors include those known collectively as the "gatrans". Particular gatrans which may be mentioned include HOOC—CH$_2$—(R)Cha-Pic-Nag-H (known as inogatran) and HOOC—CH$_2$—(R)Cgl-Aze-Pab-H (known as melagatran) (see International Patent Application WO 93/11152 and WO 94/29336, respectively, and the lists of abbreviations contained therein).

International Patent Application WO 97/23499 discloses a number of compounds which have been found to be useful as prodrugs of thrombin inhibitors. Said prodrugs have the general formula wherein $R^a$ represents H, benzyl or $C_{1-10}$alkyl, $R_b$ (which replaces one of the hydrogen atoms in the amidino unit of Pab-H) represents OH, OC(O)$R^c$ or C(O)O$R^d$, $R^c$ represents $C_{1-17}$ alkyl, phenyl or 2-naphthyl and $R^d$ represents $C_{1-12}$ alkyl, phenyl, $C_{1-3}$ alkylphenyl, or 2-naphthyl. Preferred compounds include $R^a$ OOC—CH$_2$—(R)Cgl-Aze-Pab-OH, wherein $R^a$ represents benzyl or $C_{1-10}$alkyl, e.g. ethyl or isopropyl, especially EtOOC—CH$_2$(R)Cgl-Aze-Pab-OH. The active thrombin inhibitors themselves are disclosed in WO 94/29336.

Pharmaceutical Formulations

The present invention relates to pharmaceutical compositions containing a CPU inhibitor and a thrombin inhibitor, or pharmaceutically acceptable salts thereof, as active ingredients.

Preferred combinations of a CPU inhibitor and a thrombin inhibitor are those where the CPU inhibitor is a compound of general formula I or II and the thrombin inhibitor is HOOC—CH$_2$—(R)Cgl-Aze-Pab-H, derivatives or prodrugs thereof, particularly EtOOCCH$_2$—(R)Cgl-Aze-Pab-OH.

Suitable formulations for use with HOOC—CH$_2$—(R) Cgl-Aze-Pab-H, derivatives and prodrugs thereof are described in the literature, for example as described in inter alia international patent applications WO 94/29336, WO 96/14084, WO 96/16671, WO 97/23499, WO 97/39770, WO 97/45138, WO 98/16252, WO 99/27912 and WO 99/27913, the disclosures in which documents are hereby incorporated by reference.

In the present invention, the formulation and/or kits of parts may comprise two or more CPU inhibitors in combination with a thrombin inhibitor, two or more thrombin inhibitors in combination with a CPU inhibitor or any combination thereof. Two or more inhibitors include combinations of an active ingredient and one of its prodrugs.

For clinical use, the CPU inhibitor and the thrombin inhibitor are formulated into a pharmaceutical formulation for oral, intravenous, subcutaneous, tracheal, bronchial, intranasal, pulmonary, transdermal, buccal, rectal, parenteral or some other mode of administration. The pharmaceutical formulation contains the inhibitors in admixture with a pharmaceutically acceptable adjuvant, diluent and/or carrier.

The total amount of active ingredients suitably is in the range of from about 0.1% (w/w) to about 95% (w/w) of the formulation, suitably from 0.5% to 50% (w/w) and preferably from 1% to 25% (w/w).

The molar ratio between the CPU inhibitor and the thrombin inhibitor may be in the range of from about 1000:1 to about 1:1000. The molar ratio between the CPU inhibitor and the thrombin inhibitor lies suitably in the range of from 300:1 to 1:300, and preferably from 50:1 to 1:50.

In the preparation of the pharmaceutical formulations of the present invention the active ingredients may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture may then be processed into granules or pressed into tablets.

The active ingredients may be separately premixed with the other non-active ingredients, before being mixed to form a formulation. The active ingredients may also be mixed with each other, before being mixed with the non-active ingredients to form a formulation.

Soft gelatine capsules may be prepared with capsules containing a mixture of the active ingredients of the invention, vegetable oil, fat, or other suitable vehicle for soft gelatine capsules. Hard gelatine capsules may contain granules of the active ingredients. Hard gelatine capsules may also contain the active ingredients in combination with solid powdered ingredients such as lactose, saccharose, sorbitol, mannitol, potato starch, corn starch, amylopectin, cellulose derivatives or gelatine.

Dosage units for rectal administration may be prepared (i) in the form of suppositories which contain the active substance mixed with a neutral fat base; (ii) in the form of a gelatine rectal capsule which contains the active substance in a mixture with a vegetable oil, paraffin oil or other suitable vehicle for gelatine rectal capsules; (iii) in the form of a ready-made micro enema; or (iv) in the form of a dry micro enema formulation to be reconstituted in a suitable solvent just prior to administration.

Liquid preparations may be prepared in the form of syrups or suspensions, e.g. solutions or suspensions containing the active ingredients and the remainder consisting, for example, of sugar or sugar alcohols and a mixture of ethanol, water, glycerol, propylene glycol and polyethylene glycol. If desired, such liquid preparations may contain coloring agents, flavoring agents, preservatives, saccharine and carboxymethyl cellulose or other thickening agents. Liquid preparations may also be prepared in the form of a dry powder to be reconstituted with a suitable solvent prior to use.

Solutions for parenteral administration may be prepared as a solution of a formulation of the invention in a pharmaceutically acceptable solvent. These solutions may also contain stabilizing ingredients, preservatives and/or buffering ingredients. Solutions for parenteral administration may also be prepared as a dry preparation to by reconstituted with a suitable solvent before use.

The dose of the compound to be administered will depend on the relevant indication, the age, weight and sex of the patient and may be determined by a physician. The dosage will preferably be in the range of from 0.01 mg/kg to 10 mg/kg.

The typical daily dose of the active ingredients varies within a wide range and will depend on various factors such as the relevant indication, the route of administration, the age, weight and sex of the patient and may be determined by a physician. In general, oral and parenteral dosages will be in the range of 0.1 to 1,000 mg per day of total active ingredients.

In the present invention, "a therapeutically effective total amount" relates to a total amount of the CPU inhibitor and the thrombin inhibitor which when given in combination gives a therapeutic effect, even though each amount when given separately may be less than the therapeutically effective amount.

Medical and Pharmaceutical Use

Also provided according to the present invention are formulations and kits of parts for use in medical therapy; the use of formulations of the present invention in the manufacture of medicaments for use in the treatment of a condition in which inhibition of thrombin and/or inhibition of CPU are required or desired, and methods of medical treatment or comprising the administration of a therapeutically effective total amount of a CPU inhibitor and a thrombin inhibitor of the present invention to a patient suffering from, or susceptible to, a condition in which inhibition of thrombin and/or inhibition of CPU are required or desired.

The CPU inhibitor and the thrombin inhibitor can be administered sequentially, separately and/or simultaneously. Furthermore, the CPU inhibitor can be administered prior to the administration of the thrombin inhibitor or vice versa.

The term 'medical therapy' as used herein is intended to include prophylactic, diagnostic and therapeutic regimens carried out in vivo or ex vivo on humans or other mammals.

The formulations of the invention contain an inhibitor of CPU and an inhibitor of thrombin, either as such or, in the case of prodrugs, after administration. The formulations of the invention are thus expected to be useful in those conditions where inhibition of CPU and/or inhibition of thrombin are beneficial, such as in the treatment of thrombosis and hypercoagulability in blood and tissues of mammals, including man.

The term "condition in which inhibition of thrombin is required or desired" will be understood by those skilled in the art to include the following:

the treatment and/or prophylaxis of thrombosis and hypercoagulability in blood and tissues of animals including man. It is known that hypercoagulability may lead to thromboembolic diseases. Conditions associated with hypercoagulability and thromboembolic diseases which may be mentioned include inherited or acquired activated protein C resistance, such as the factor V-mutation (factor V Leiden), and inherited or acquired deficiencies in antithrombin III, protein C, protein S, heparin cofactor II. Other conditions known to be associated with hypercoagulability and thromboembolic disease include circulating antiphospholipid antibodies (Lupus anticoagulant), homocysteinemia, heparin-induced thrombocytopenia and defects in fibrinolysis.

The treatment of conditions where there is an undesirable excess of thrombin without signs of hypercoagulability, for example in neurodegenerative diseases such as Alzheimer's disease.

Particular disease states which may be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis) and systemic embolism usually from the atrium during arterial fibrillation or from the left ventricle after transmural myocardial infarction, or caused by congestive heart failure; prophylaxis of re-occlusion (i.e. thrombosis) after thrombolysis, percutaneous trans-luminal angioplasty (PTA) and coronary bypass operations; the prevention of re-thrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease, cerebral arterial disease, peripheral arterial disease, reperfusion damage, and restenosis after percutaneous trans-luminal angioplasty (PTA).

EXAMPLES

The following Examples are intended to illustrate, but in no way limit the scope of the invention.

Materials and Methods

Materials

Batroxobin No. 520 CRY (American Diagnostica Inc., Greenwich, Conn., USA) was kept at 8° C. both while lyophilized and when dissolved in saline to a concentration of 10 BU/ml. It was used within 5 days in the experiments. The remaining drug was freezed and kept at 20° C. for a maximum of 30 days.

Endotoxin L-3129 (Sigma, St. Louis, Mo., USA) was dissolved in saline to a concentration of 50 µg/ml. A fresh solution was prepared for each experiment.

$^{125}$I-labelled human fibrinogen (Amersham, Little Chalfont, Buck., UK) was stored at 8° C. while lyophilized. After dissolving in saline/aq.dest. (80/20 v/v) to a stock solution of approx. 0.8 MBq/ml (20 µCi/ml) it was divided into aliquots (one for each experiment), quickly freezed and stored at −20° C. It was used in the experiments within 14 days after the production date.

Inactin, thiobutabarbital sodium salt (Research Biochemicals International, Natick, USA) was dissolved in saline/aq.dest. (50/50 v/v) to a concentration of 50 mg/ml.

The thrombin inhibitor inogatran was dissolved in 40% (w/w) cyclodextrin (HPβCD) to a concentration of 5 mg/ml and stored at −20° C. It was further diluted with 40% cyclo-dextrin before use in the different experiments. In the studies the drug was administered subcutaneously.

The thrombin inhibitor melagatran was dissolved in saline.

The CPU inhibitors MERGETPA and Compound A were dissolved in deoxygenated saline. The saline was deoxygenated by ultrasonication for 20 min and subsequently by passing nitrogen for another 20 min. The solutions were always fresh-made for each experiment. The CPU inhibitor was administered to the rats as an i.v. infusion for 5 min.

Animals

Male rats of the Sprague Dawley strain (Charles River, Sweden) with a body weight of 325–425 g were used in these experiments. The animals were allowed to accommodate at AstraZeneca R&D, Mölndal, Sweden for 1 week before use.

Animal Preparation

Anaesthesia was induced and maintained by Inactin 100 mg/kg i.p.

Two catheters were inserted in the left jugular vein, one for administration of $^{125}$I-fibrinogen and batroxobin and the other for administration of endotoxin and CPU inhibitor or their corresponding vehicles. A third catheter was inserted in the carotid artery for blood sampling and measurement of the mean arterial blood pressure and heart rate. To avoid blood clots in the arterial catheter a slow saline infusion (approx. 1.0 ml/kg*h) was maintained throughout the experiment. The rats were tracheotomized in order to facilitate spontaneous breathing. The body temperature was monitored and maintained at 38° C. by external heating.

Experimental Protocol

The animals were given an i.v. injection of endotoxin (50 µg/kg) at the start of the experiment. Two hours later the thrombin inhibitor or its vehicle was injected subcutaneously and another 15 min later $^{125}$I-fibrinogen (0.04 MBq) was given as an i.v. injection. An infusion lasting for five minutes of the CPU-inhibitor or its vehicle was started after 5 min. After 5 min, batroxobin (10 BU/kg) was given as an i.v. bolus injection for one minute.

Blood samples for determination of $^{125}$I-content were taken in all experiments just before and 5, 20 and 30 min after the batroxobin administration. At the end of the experiment the lungs were excised, the tissue was gently washed in saline and thereafter blotted and weighed. The $^{125}$I-content in the tissue and blood samples was determined, using a Wallac 1282 Compugamma counter. The $^{125}$I-concentration in plasma and in the lungs was expressed as a percentage of the radioactivity in the reference arterial blood sample taken just prior to the batroxobin injection.

Example 1

The CPU inhibitor mergetpa (DL-2-mercaptomethyl-3-guanidinoethylthiopropanoic acid) known e.g. from Biochimica & Biophysica Acta 1034 (1990) 86–92 was used in combination with the thrombin inibitor inogatran.

The results of the experiments are evident from Table I. The results are expressed as the remaining fibrin in the lung after treatment, i.e. 100% is equal to no effect. n denotes the number of experiments (rats).

TABLE I

Effect on lung fibrin deposition in the anaesthetized rat in experiments with MERGETPA and/or inogatran

| CPU inhibitor | | Thrombin Inhibitor | | CPU Thrombin inhibitor + inhibitor | |
|---|---|---|---|---|---|
| Dose (μmol/kg) | Remaining fibrin after treatment (% SD) | Dose (μmol/kg) | Remaining fibrin after treatment (% SD) | Dose (μmol/kg) | Remaining fibrin after treatment (% SD) |
| 2.1 | — | 0.6 | — | 2.1 + 0.6 | 100 ± 23.9 n = 6 |
| 4.2 | — | 1.2 | — | 4.2 + 1.2 | 62 ± 21.9 n = 6 |
| 8.4 | 90 ± 18.1 n = 6 | 2.3 | 94 ± 20.2 n = 6 | 8.4 + 2.3 | 26 ± 13.3 n = 9 |
| 21.1 | 37 ± 19.3 n = 6 | 3.4 | 72 ± 23.6 n = 6 | — | — |
| 33.7 | 23 ± 17.3 n = 6 | 5.7 | 41 ± 20.3 n = 6 | — | — |
| — | — | 17.2 | 39 ± 15.9 n = 6 | — | — |

It is evident from Table I, that administration of the combination of a CPU inhibitor and a thrombin inhibitor is superior to administration of either inhibitor as regards remaining fibrin after treatment.

Example 2

The CPU inhibitor (3-(6-amino-pyridin-3-yl)-2-mercaptomethyl-propanoic acid) (Compound A) was used in combination with the thrombin inibitor melagatran.

The results of the experiments are evident from Table II. The results are expressed as the remaining fibrin in the lung after treatment, i.e. 100% is equal to no effect. n denotes the number of experiments (rats).

TABLE II

Effect on lung fibrin deposition in the anaesthetized rat in experiments with compound A and/or melagatran

| CPU Inhibitor | | Thrombin inhibitor | | CPU Thrombin inhibitor + inhibitor | |
|---|---|---|---|---|---|
| Dose (μmol/kg) | Remaining fibrin after treatment (% ± SD) | Dose (μmol/kg) | Remaining fibrin after treatment (% ± SD) | Dose (μmol/kg) | Remaining fibrin after treatment (% ± SD) |
| 0.20 | 100 ± 25.8 n = 8 | 0.23 | 97 ± 12.4 n = 6 | 0.20 + 0.23 | 75 ± 35.2 n = 5 |
| 0.28 | 88 ± 23.2 n = 4 | 0.35 | 77 ± 22.4 n = 4 | 0.28 + 0.35 | 19 ± 13.9 n = 8 |
| 0.4 | 87 ± 50.6 n = 6 | 0.58 | 62 ± 17.0 n = 2 | — | — |
| 2.0 | 49 ± 30.0 n = 7 | 1.75 | 31 ± 13.3 n = 4 | — | — |
| 4.0 | 15 ± 9.3 n = 4 | 3.5 | 55 ± 21.7 n = 4 | — | — |
| 20.0 | 7 ± 1.4 n = 2 | — | — | — | — |

It is evident from Table II, that administration of the combination of a CPU inhibitor and a thrombin inhibitor is superior to administration of either inhibitor as regards remaining fibrin after treatment.

Example 3

The CPU inhibitor (3-(6-amino-pyridin-3-yl)-2-mercaptomethyl-propanoic acid) (Compound A) was used in combination with the thrombin inibitor melagatran.

The results of the experiments are evident from Table III. The results are expressed as the remaining fibrin in the lung after treatment, i.e. 100% is equal to no effect. n denotes the number of experiments (rats).

TABLE III

Proof of the synergistic effect on lung fibrin deposition in the anaesthetized rat in experiments with compound A and melagatran

| CPU inhibitor (compound A) | | Thrombin inhibitor (melagatran) | | CPU inhibitor + Thrombin inhibitor | |
|---|---|---|---|---|---|
| Dose (μmol/kg) | Remaining fibrin after treatment (% ± SD) | Dose (μmol/kg) | Remaining fibrin after treatment (% ± SD) | Dose (μmol/kg) | Remaining fibrin after treatment (% ± SD) |
| 0.20 | 97 ± 24.1 n = 10 | 0.18 | 110 ± 15.2 n = 3 | — | — |
| 0.20 | 97 ± 24.1 n = 10 | 0.23 | 98 ± 11.5 n = 7 | 0.20 + 0.23 | 70 ± 33.8 n = 6 |
| 0.20 | 97 ± 24.1 n = 10 | 0.30 | 87 ± 27.6 n = 3 | 0.20 + 0.30 | 51 ± 33.3 n = 5 |
| 0.20 | 97 ± 24.1 n = 10 | 0.35 | 77 ± 22.4 n = 4 | 0.20 + 0.35 | 35 ± 24.3 n = 5 |
| 0.20 | 97 ± 24.1 n = 10 | 0.70 | — | 0.20 + 0.70 | 18 ± 12.7 n = 2 |
| 0.28 | 81 ± 24.5 n = 5 | 0.18 | 110 ± 15.2 n = 3 | 0.28 + 0.18 | 71 ± 33.2 n = 5 |
| 0.28 | 81 ± 24.5 n = 5 | 0.23 | 98 ± 11.5 n = 7 | 0.28 + 0.23 | 42 ± 28.3 n = 5 |
| 0.28 | 81 ± 24.5 n = 5 | 0.30 | 87 ± 27.6 n = 3 | — | — |
| 0.28 | 81 ± 24.5 n = 5 | 0.35 | 77 ± 22.4 n = 4 | 0.28 + 0.35 | 20 ± 13.3 n = 9 |
| 0.28 | 81 ± 24.5 n = 5 | 0.42 | — | 0.28 + 0.42 | 9 ± 3.5 n = 2 |

Figure 1:
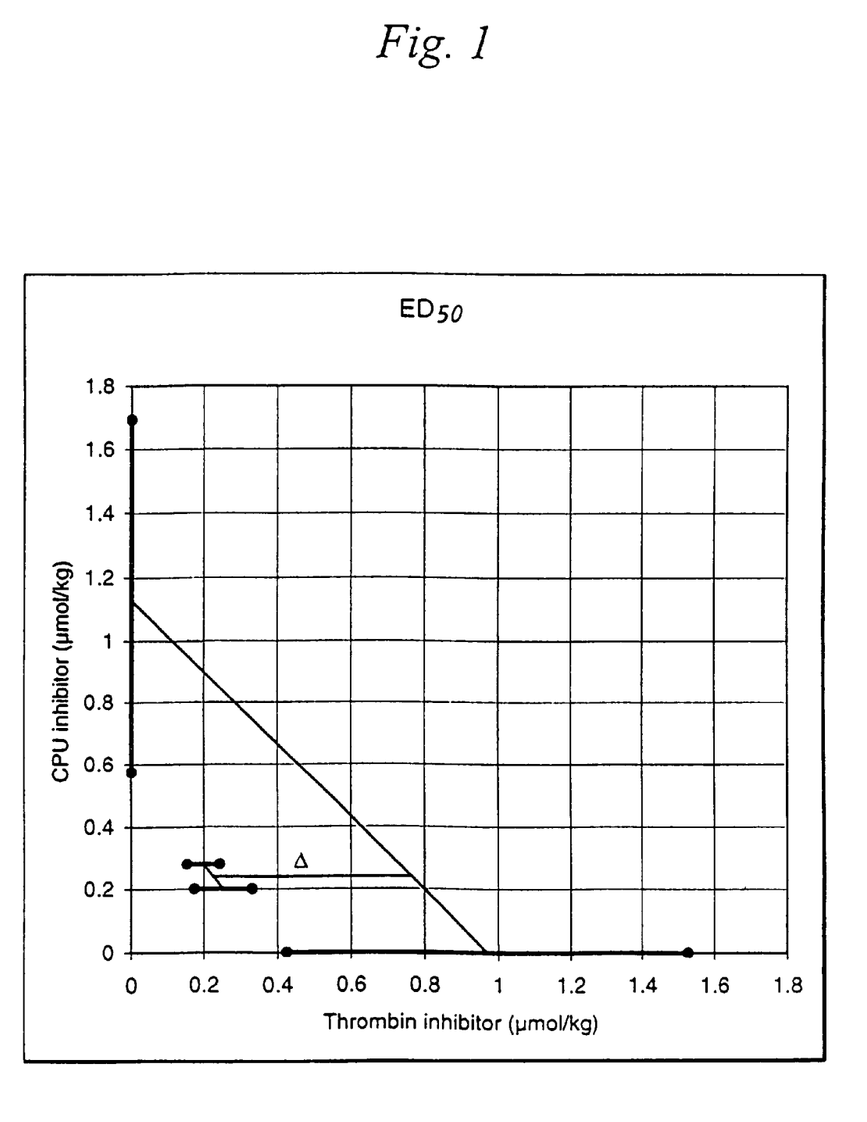
FIG. 1 provides a demonstration of the synergistic effect of a combination of compound A and melagatran on reduction of fibrin deposition in lungs of Sprague Dawley rats.

For each of the four different dose combinations, only CPU inhibitor, only thrombin inhibitor, thrombin inhibitor together with CPU inhibitor at 0.2 and 0.28 μmol/kg respectively, separate E-max models were fitted. The models were fitted on a logarithmic scale giving estimates of the median effective dose, i.e., the dose where half of the population has 50% effect. In FIG. 1 the confidence intervals of these $ED_{50}$'s are plotted.

In absence of a synergistic effect the $ED_{50}$ for a combination of CPU inhibitor and thrombin inhibitor would lie on the line connecting the $ED_{50}$'s for each drug given alone (see FIG. 1). In order to estimate the synergistic effect, all four dose combinations were fitted to an E-max model, where the $ED_{50}$ for the thrombin inhibitor together with the CPU inhibitor at 0.2 and 0.28 μmol/kg respectively was modelled using the parameter Δ, as described in the figure. The parameter Δ was estimated to 0.52 with a 95% confidence interval [0.116, 0.934], and was statistically significant from 0, p<0.001.

Abbreviations
Ac=acetate
AIBN=(α,α'-azoisobutyronitrile
Aze=(S)-azetidine-2-carboxylic acid
Bn=benzyl
Bu=butyl
BU=batroxobin units as defined by American Diagnostica Inc., USA)
Bz=benzoyl
Cha=β-cyclohexyl alanine
Cgl=(S)-cyclohexyl glycine
DCC=dicyclohexylcarbodiimide
DIAD=diisopropyl azodicarboxylate
DIPEA=diisopropylethylamine
DMAP=N,N-dimethyl amino pyridine
EDC=1-(3-dimethylaminopropyl)-3-ethylcarbodiimide
EtOH=ethanol
HMDS=hexamethyl disilazane
HOAc=acetic acid
HOBt=1-hydroxybenzotriazol
HPβCD=hydroxypropyl β-cyclodextrin
i.p.=intraperitoneal
i.v.=intravenous
KHMDS=potassium bis(trimethylsilyl)amide
LDA=lithium diisopropylamide
Me=methyl
MeOH=methanol
Nag-H=noragmatine
Pab-H=1-amidino-4-aminomethyl benzene
Ph=phenyl
Pic=pipecolinic acid
PMB=4-methoxybenzyl
PyBOP=(benzotriazol-1-yloxy)tripyrrolidinophosphonium hexafluorophosphate
SD=standard deviation
TEA=triethylamine
TFA=trifluoroacetic acid
THF=tetrahydrofuran
TMSCN=trimethylsilylcyanide
Tos(yl)=toluene-4-sulfonyl

What is claimed is:

1. A formulation comprising:
   (i) an inhibitor of carboxypeptidase U or a pharmaceutically acceptable salt thereof; and
   (ii) a thrombin inhibitor or an ester or prodrug thereof, or a salt and/or solvate of any of these, in admixture with a pharmaceutically acceptable adjuvant, diluent, or carrier, wherein the inhibitor of carboxypeptidase U is a compound of formula I or a pharmaceutically acceptable salt or solvate thereof, or a solvate of such a salt,
wherein:
   $R_1$ s selected from the group consisting of:
      cycloalkyl, substituted with one or more basic groups;
      heterocyclyl, comprising at least one nitrogen atom, and substituted with one or more basic groups;
      heterocyclyl, comprising at least one hetero atom selected from S or O, and substituted with one or more basic groups; and
      aryl, substituted with one or more basic groups;
   $R_2$ is selected from the group consisting of H, acyl, acylamino, alkyl, alkylcarbamoyl, alkylthio, alkoxy, aroyl, aroylamino, aryloxy, arylthio, amidino, amino, aryl, carbamoyl, carboxy, cyano, cycloalkyl, formyl, guanidino, halogen, heterocyclyl, hydroxy, nitro, thiol, a $Z_2N$—CO—o—group, a ZO—CO—NZ— group, and a $Z_2N$—CO—NZ— group;
   $R_3$ is selected from the group consisting of $COOR_5$, $SO(OR_5)$, $SO_3R_5$, $P=O(OR_5)_2$, $B(OR_5)_2$, $P=OR_5(OR_5)$, tetrazole, and a carboxylic acid isostere;
   $R_4$ is SH, S—CO—$C_1$, —C alkyl, or S—CO-aryl;
   $R_5$ is H, $C_1$–$C_6$ alkyl, or aryl;
   $R_6$ is H or $C_1$–$C_6$ alkyl;
   X is selected from the group consisting of O, S, SO, $SO_2$, $C(Z)_2$, N(Z), $NR_6SO_2$, and $SO_2NR_6$;
   Y is $C(Z)_2$; and
   Z is independently selected from the group consisting of H, $C_1$–$c_6$ alkyl, aryl, cycloalkyl and heterocyclyl.

2. The formulation according to claim 1, wherein the thrombin inhibitor is a low molecular weight thrombin inhibitor.

3. The formulation according to claim 2, wherein the low molecular weight thrombin inhibitor is a peptide-based, amino acid-based, and/or peptide analogue-based, thrombin inhibitor with one to four peptide linkages.

4. The formulation according to claim 3, wherein the low molecular weight thrombin inhibitor is HOOC—$CH_2$—(R)Cgl-Aze-Pab-H or a prodrug thereof.

5. The formulation according to claim 4, wherein the prodrug is EtOOC—$CH_2$—(R)Cgl-Aze-Pab-OH.

6. The formulation according to claim 1, wherein the molar ratio between the inhibitor of carboxypeptidase U and the thrombin inhibitor lies in the range of from 1000:1 to 1:1000.

7. A kit of parts comprising:
   (i) a vessel comprising an inhibitor of carboxypeptidase U, or a pharmaceutically acceptable salt thereof;
   (ii) a vessel comprising a thrombin inhibitor, or an ester or prodrug thereof, or a salt and/or solvate of any of these; and
   (iii) instructions for the sequential, separate or simultaneous administration of the inhibitors (i) and (ii) to a patient in need thereof, wherein the inhibitor of carboxypeptidase U is a compound according to claim 1.

8. The kit of parts according to claim 7, wherein the thrombin inhibitor is a low molecular weight thrombin inhibitor.

9. The kit of parts according to claim 8, wherein the low molecular weight thrombin inhibitor is a peptide-based, amino acid-based, and/or peptide analogue-based, thrombin inhibitor with one to four peptide linkages.

10. The kit of parts according to claim 9, wherein the low molecular weight thrombin inhibitor is HOOC—CH$_2$—(R)Cgl-Aze-Pab-H or a prodrug thereof.

11. The kit of parts according to claim 10, wherein the prodrug is EtOOC—CH$_2$—(R)Cgl-Aze-Pab-OH.

12. The kit of parts according to claim 7, wherein the molar ratio between the inhibitor of carboxypeptidase U and the thrombin inhibitor lies in the range of from about 1000:1 to 1:1000.

13. A kit of parts comprising:
(i) a formulation comprising an inhibitor of carboxypeptidase U, or a pharmaceutically acceptable salt thereof, in admixture with a pharmaceutically acceptable adjuvant, diluent, or carrier; and
(ii) a formulation comprising a thrombin inhibitor, or an ester or prodrug thereof, or a salt and/or solvate of any of these, in admixture with a pharmaceutically acceptable adjuvant, diluent, or carrier,
wherein inhibitors (i) and (ii) are each formulated for administration in conjunction with the other, and wherein the inhibitor of carboxypeptidase U is a compound according to claim 1.

14. The kit of parts according to claim 13, wherein inhibitors (i) and (ii) are formulated for sequential, separate or simultaneous administration.

15. The kit of parts according to claim 13, wherein the thrombin inhibitor is a low molecular weight thrombin inhibitor.

16. The kit of parts according to claim 15, wherein the low molecular weight thrombin inhibitor is a peptide-based, amino acid-based, and/or peptide analogue-based, thrombin inhibitor with one to four peptide linkages.

17. The kit of parts according to claim 16, wherein the low molecular weight thrombin inhibitor is HOOC—CH$_2$—(R)Cyl-Aze-Pab-H or a prodrug thereof.

18. The kit of parts according to claim 17, wherein the prodrug is EtOOC—CH$_2$—(R)Cgl-Aze-Pab-OH.

19. The kit of parts according to claim 13, wherein the molar ratio between the inhibitor of carboxypeptidase U and the thrombin inhibitor lies in the range of from 1000:1 to 1:1000.

20. A method for the treatment of thrombosis and/or hypercoagulability, which method comprises administering to a patient in need thereof a therapeutically effective total amount of:
(i) an inhibitor of carboxypeptidase U, or a pharmaceutically acceptable salt thereof, in admixture with a pharmaceutically acceptable adjuvant, diluent or carrier; and
(ii) a thrombin inhibitor, or an ester or prodrug thereof, or a salt and/or solvate of any of these, in admixture with a pharmaceutically acceptable adjuvant, diluent, or carrier, wherein the inhibitor of carboxypeptidase U is a compound according to claim 1.

21. The method according to claim 20, wherein the administration of inhibitors (i) and (ii) is sequential, separate or simultaneous.

22. The method according to claim 20, wherein the thrombin inhibitor is a low molecular weight thrombin inhibitor.

23. The method according to claim 22, wherein the low molecular weight thrombin inhibitor is a peptide-based, amino acid-based, and/or peptide analogue-based, thrombin inhibitor with one to four peptide linkages.

24. The method according to claim 23, wherein the low molecular weight thrombin inhibitor is HOOC—CH$_2$—(R)Cgl-Aze-Pab-H or a prodrug thereof.

25. The method according to claim 24, wherein the prodrug is EtOOC—CH$_2$—(R)Cgl-Aze-Pab-OH.

26. The method according to claim 20, wherein the molar ratio between the inhibitor of carboxypeptidase U and the thrombin inhibitor lies in the range of from 1000:1 to 1:1000.

27. A method for treatment of thrombosis and/or hypercoagulability, which method comprises administering to a patient in need thereof a formulation according to claim 1.

28. The formulation according to claim 1, wherein the basic group is selected from the group consisting of amino, amidino, and guanidino.

29. The formulation according to claim 1, wherein the molar ratio between the inhibitor of carboxypeptidase U and the thrombin inhibitor lies in the range of from about 50:1 to about 1:50.

30. The kit of parts according to claim 7, wherein the molar ratio between the inhibitor of carboxypeptidase U and the thrombin inhibitor lies in the range from 50:1 to 1:50.

31. The kit of parts according to claim 13, wherein the molar ratio between the inhibitor of carboxypeptidase U and the thrombin inhibitor lies in the range of from 50:1 to 1:50.

32. The method according to claim 20, wherein the molar ratio between the inhibitor of carboxypeptidase U and the thrombin inhibitor lies in the range of from 50:1 to 1:50.

33. A method for reducing the risk of thrombosis and/or hypercoagulability, which method comprises administering to a patient a therapeutically effective total amount of:
(i) an inhibitor of carboxypeptidase U, or a pharmaceutically acceptable salt thereof, in admixture with a pharmaceutically acceptable adjuvant, diluent or carrier; and
(ii) a thrombin inhibitor, or an ester or prodrug thereof, or a salt and/or solvate of any of these, in admixture with a pharmaceutically acceptable adjuvant, diluent, or carrier, wherein the inhibitor of carboxypeptidase U is a compound according to claim 1.

* * * * *